United States Patent [19]

Rice

[11] Patent Number: 5,397,565
[45] Date of Patent: Mar. 14, 1995

[54] LOTION FOR HOOVES

[76] Inventor: Winston Rice, Box 40, Site 2, R.R. #8, Calgary, Alberta, Canada, T2J 2T9

[21] Appl. No.: 239,292

[22] Filed: May 6, 1994

[51] Int. Cl.⁶ .............................................. A61K 7/04
[52] U.S. Cl. ..................................... 424/61; 424/401; 424/523
[58] Field of Search .................... 424/401, 61, 523

[56] References Cited

U.S. PATENT DOCUMENTS

| | | | |
|---|---|---|---|
| 3,887,702 | 6/1975 | Baldwin | 424/61 |
| 4,070,451 | 1/1978 | Price | 424/61 |
| 4,447,418 | 5/1984 | Maddoux | 424/165 |
| 4,822,595 | 4/1989 | Corliss et al. | 424/61 |
| 4,996,043 | 2/1991 | Adamich-Saltman | 424/61 |
| 5,079,003 | 1/1992 | Scaffidi | 424/401 |
| 5,147,651 | 9/1992 | Hobson et al. | 424/443 |

*Primary Examiner*—Thurman K. Page
*Assistant Examiner*—Jyothsna Venkat
*Attorney, Agent, or Firm*—Anthony R. Lambert

[57] ABSTRACT

A lotion for hooves is described that includes the following ingredients expressed as a percentage of volume. Fish oil should represent 20 to 81 percent of total volume; pine tar 1 to 45 percent; and-propylene glycerol 15 to 36 percent. The remainder of the lotion, 3 to 20 percent, should consist of a compatible emulsifying agent for maintaining pine tar in emulsion. By adjusting the proportions of ingredients the described lotion can be adapted to suit seasonal humidity.

3 Claims, No Drawings

LOTION FOR HOOVES

BACKGROUND OF THE INVENTION

A variety of lotions have been developed for the care of domestic hoofed animals. The role these lotions are intended to play vary with weather conditions. In arid weather a moisturizing lotion is required. In humid weather the lotion must serve as a moisture retardant; keeping moisture and dampness out of the hooves.

The ingredients of a moisturizing lotion generally differ from the ingredients of a moisture retarding lotion. This makes it difficult to make adjustments to the lotion as weather conditions change from arid to humid and to the vast range of conditions inbetween.

SUMMARY OF THE INVENTION

What is required is a lotion that can be adjusted to suit the humidity by altering the proportions of ingredients.

According to the present invention there is provided a lotion for hooves. The lotion includes the following ingredients expressed as a percentage of volume. Fish oil should represent 20 to 81 percent of total volume; pine tar 1 to 45 percent; and propylene glycerol 15 to 36 percent. The remainder of the lotion, 3 to 20 percent, should consist of a compatible emulsifying agent for maintaining pine tar in emulsion.

Pine tar acts as a moisture retardant. As the humidity increases the proportion of pine tar should be increased. When the proportion of pine tar is increased the proportion of the emulsifying agent should also be increased to ensure that the lotion is consistent. Fish oil has moisturizing properties. Propylene glycerol is a humectant that is compatible with fish oil and serves as a "conditioner" by controlling the odour of the fish oil. As the humidity decreases the proportion of pine tar should be increased. When the proportion of fish oil is increased the proportion of propylene glycerol should also be increased. It will be appreciated that the lotion, as described above, can be adjusted to suit the humidity. The preferred emulsifying agent for use with the pine tar is a mixture of corn oil and sunflower seed oil; although other vegetable or cereal oils may be substituted.

DETAILED DESCRIPTION OF THE PREFERRED EMBODIMENT

The preferred lotion for hooves, with ingredients expressed as a percentage of volume, includes 20 to 81 percent fish oil; 1 to 45 percent pine tar; 15 to 36 propylene glycerol; 1.5 to 10 percent corn oil; and 1.5 to 10 percent sunflower seed oil.

The role of the ingredients will now be described. Pine tar acts as a moisture retardant. As the humidity increases the proportion of pine tar should be increased. If the percentage of pine tar in a mixture is reduced below 1 percent, the pine tar is no longer playing a useful role in the lotion. Conversely, if the percentage of pine tar is increased above 45 percent its moisture retardant qualities will be destroy the utility of the lotion. When the proportion of pine tar is increased the proportion of the corn oil and sunflower oil should also be increased to ensure that the lotion is consistent. Fish oil has moisturizing properties. If the percentage of fish oil is reduced below 20 percent, the fish oil is no longer effectively serving to moisturize the hooves. Conversely, if the percentage of fish oil is increased above 81 percent, too great a proportion of the other ingredients are being removed to the detriment of the lotion. Propylene glycerol is a humectant that is compatible with fish oil and serves as a "conditioner" by controlling the odour of the fish oil. As the humidity decreases the proportion of pine tar should be increased. When the proportion of fish oil is increased the proportion of propylene glycerol should also be increased.

The general useful ranges having been set forth, some sample formulas will now be discussed in order to demonstrate the manner in which the lotion is adjusted to suit the humidity.

Humid Weather

A lotion for hooves for humid weather includes: 20 to 30 percent fish oil; 35 to 45 percent pine tar; 15 to 20 percent propylene glycerol; 7 to 10 percent corn oil; and 7 to 10 percent sunflower seed oil. It should be noted that this lotion contains a high percentage of pine tar with it's moisture retardant properties. It should also be noted that the percentage of corn oil and sunflower seed oil is relatively high in order to provide a consistent mixture of the fish oil with the pine tar.

Arid Weather

A lotion for hooves for arid weather includes: 60 to 70 percent fish oil; 1 to 5 percent pine tar; 30 to 36 percent propylene glycerol; 1.5 to 4 percent corn oil; and 1.5 to 4 percent sunflower seed oil. It should be noted that this lotion contains a high percentage of fish oil and that the percentage of pine tar is greatly reduced. The change in the proportions of fish oil and pine tar leads to an increase in the amount of propylene glycerol and a decrease in the amount of corn oil and sunflower seed oil.

It should be noted that other vegetable and cereal oils can be substituted for the preferred mixture of corn oil and sunflower seed oil. It will also be apparent to one skilled in the art that modifications may be made to the illustrated embodiment without departing from the spirit and scope of the invention as defined by the claims.

The embodiments of the invention in which an exclusive property or privilege is claimed are as follows:

1. A lotion for hooves, comprising the following ingredients expressed as a percentage of volume:
   a. 20 to 81 percent fish oil;
   b. 1 to 45 percent pine tar;
   c. 15 to 36 percent propylene glycerol;
   d. 3 to 20 percent of an emulsifying agent for maintaining pine tar in emulsion. Selected from the group consisting of corn oil and sunflower seed oil.

2. A lotion for hooves, comprising the following ingredients expressed as a percentage of volume:
   a. 20 to 30 percent fish oil;
   b. 35 to 45 percent pine tar;
   c. 15 to 20 percent propylene glycerol;
   d. 7 to 10 percent corn oil; and
   e. 7 to 10 percent sunflower seed oil.

3. A lotion for hooves, comprising the following ingredients expressed as a percentage of volume:
   a. 60 to 70 percent fish oil;
   b. 1 to 5 percent pine tar;
   c. 30 to 36 percent propylene glycerol;
   d. 1.5 to 4 percent corn oil; and
   e. 1.5 to 4 percent sunflower seed oil.

* * * * *